US011083692B2

(12) United States Patent
Stefik et al.

(10) Patent No.: US 11,083,692 B2
(45) Date of Patent: Aug. 10, 2021

(54) ULTRASONIC CAVITATION ENABLED TUNING OF PERSISTENT MICELLES

(71) Applicant: UNIVERSITY OF SOUTH CAROLINA, Columbia, SC (US)

(72) Inventors: Morgan Stefik, Columbia, SC (US); Hasala N. Lokupitiya, Columbia, SC (US)

(73) Assignee: University of South Carolina, Columbia, SC (US)

( * ) Notice: Subject to any disclaimer, the term of this patent is extended or adjusted under 35 U.S.C. 154(b) by 0 days.

(21) Appl. No.: 16/499,408

(22) PCT Filed: Sep. 6, 2017

(86) PCT No.: PCT/US2017/050158
§ 371 (c)(1),
(2) Date: Sep. 30, 2019

(87) PCT Pub. No.: WO2018/186903
PCT Pub. Date: Oct. 11, 2018

(65) Prior Publication Data
US 2020/0146987 A1    May 14, 2020

Related U.S. Application Data

(60) Provisional application No. 62/481,822, filed on Apr. 5, 2017.

(51) Int. Cl.
*A61K 9/107* (2006.01)
*A61K 47/32* (2006.01)
(Continued)

(52) U.S. Cl.
CPC ............ *A61K 9/1075* (2013.01); *A61K 47/32* (2013.01); *B01J 13/08* (2013.01); *C08J 5/00* (2013.01); *C08J 2353/00* (2013.01)

(58) Field of Classification Search
CPC ....... A61K 9/1075; A61K 47/32; B01J 13/08; C08J 5/00; C08J 2353/00; C23C 18/1216
See application file for complete search history.

(56) References Cited

U.S. PATENT DOCUMENTS

| 2005/0025830 | A1 | 2/2005 | Bruinewoud et al. | |
|---|---|---|---|---|
| 2008/0311045 | A1* | 12/2008 | Hardy | A61K 9/5146 424/9.3 |
| 2012/0263938 | A1* | 10/2012 | Paul | C23C 18/1279 428/312.8 |

OTHER PUBLICATIONS

Morov, Common Solvents: Table of Properties. (Year: 2016).*
(Continued)

*Primary Examiner* — Carlos A Azpuru
(74) *Attorney, Agent, or Firm* — Dority & Manning, P.A.

(57) ABSTRACT

A method to quickly adjust the size of micelles and then return the micelles to a persistent state is provided. Specifically, the present invention is directed to a method for block copolymer micelle growth under high-χN solution conditions where ultrasonic cavitation facilitates rapid solution-gas interface production that accelerates micelle growth by an order of magnitude over other methods such as vortexing. The persistent micelles formed by the method of the present invention can then be used for controlled delivery of dispersions in organic electronic coatings, paint, or drug delivery applications and can also be used to control the pore size of films that include an oxide, a nitride, a carbide, a metal, or a carbon material.

19 Claims, 9 Drawing Sheets

(51) Int. Cl.
B01J 13/08 (2006.01)
C08J 5/00 (2006.01)

(56) References Cited

OTHER PUBLICATIONS

Alexandridis, et al. "Amphiphilic block copolymers: self-assembly and applications" *Elsevier* (2000).
Aniansson, et al. "A Correction and Improvement of 'Kinetics of step-wise micelle association'" *J. Phys. Chem.* 79(8) (1975) pp. 857-858.
Bastakoti, et al. "Asymmetric block copolymers for supramolecular templating of inorganic nanospace materials" *Small* 11 (2015) pp. 1992-2002.
Blanazs, et al. "Self-Assembled Block Copolymer Aggregates: From Micelles to Vesicles and their Biological Applications" *Macromol. Rapid Commun.* 30 (2009) pp. 267-277.
Cabral, et al. "Accumulation of sub-100 nm polymeric micelles in poorly permeable tumours depends on size" *Nature Nanotechn.* 6 (2011) pp. 815-823.
Choi, et al. "Small-angle X-ray scattering of concentration dependent structures in block copolymer solutions" *Macromolecules* 47(22) (2014) pp. 7978-7986.
Choi, et al. "Mechanism of molecular exchange in diblock copolymer micelles: hypersensitivity to core chain length" *Phys. Rev. Lett.* 104:047802 (2010) pp. 1-4.
Denkova, et al. "Non-equilibrium dynamics of block copolymer micelles in solution: recent insights and open questions" *Soft Matt.* 6 (2010) pp. 2351-2357.
Esselink, et al. "Redistribution of block copolymer chains between mixed micelles in solution" *Macromolecules* 31(5) (1998) pp. 4873-4878.
Guerrero-Sanchez, et al. "Structure—property study of diblock copolymer micelles: core and corona radius with varying composition and degree of polymerization" *Macromolecules* 38 (2005) pp. 10185-10191.
Halperin, et al. "Polymeric micelles: their relaxation kinetics" *Macromolecules* 22 (1989) pp. 2403-2412.
Hayward, et al. "Tailored assemblies of block copolymers in solution: it is all about the process" *Macromolecules* 43 (2010) pp. 3577-3584.
Jiang, et al. "Tunable-Sized Polymeric Micelles and Their Assembly for the Preparation of Large Mesoporous Platinum Nanoparticles" *Angew. Chem.* 55 (2016) pp. 10037-10041.
Kabanov, et al. "Pluronic® block copolymers as novel polymer therapeutics for drug and gene delivery" *J. Contr. Rel.* 82 (2002) pp. 189-212.
Kakizawa, et al. "Block copolymer micelles for delivery of gene and related compounds" *Adv. Drug Deliv. Rev.* 54 (2002) pp. 203-222.
Kataoka, et al. "Block copolymer micelles for drug delivery: design, characterization and biological significance" *Adv. Drug Deliv. Rev.* 47(1) (2001) pp. 113-131.
Kelley, et al. "Size evolution of highly amphiphilic macromolecular solution assemblies via a distinct bimodal pathway" *Nat. Comm.* 5:3599 (2014) pp. 1-10.
Kelley, et al. "Stimuli-responsive copolymer solution and surface assemblies for biomedical applications" *Chem. Soc. Rev.* 42(17) (2013) pp. 7057-7071.
Kelley, et al. "Structural changes in block copolymer micelles induced by cosolvent mixtures" *Soft Matter* 7 (2011) pp. 7094-7102.
Lokupitiya, et al. "Cavitation-enabled rapid and tunable evolution of high-$\chi$N micelles as templates for ordered mesoporous oxides" *Nanoscale* 9(4) (2017) pp. 1319-1748.
Lu, et al. "Addition of corona block homopolymer retards chain exchange in solutions of block copolymer micelles" *Macromolecules* 49 (2016) pp. 1405-1413.
Lu, et al. "Remarkable effect of molecular architecture on chain exchange in triblock copolymer micelles" *Macromolecules* 48 (2015) pp. 2667-2676.
Lu, et al. "Chain Exchange in Binary Copolymer Micelles at Equilibrium: Confirmation of the Independent Chain Hypothesis" *ACS Macro Lett.* 2 (2013) pp. 451-455.
Lund, et al. "Kinetics of Block Copolymer Micelles Studied by Small-Angle Scattering Methods" *Adv. Polym. Sci.* 259 (2013) pp. 51-158.
Ma, et al. "Poly(methyl methacrylate)-block-poly(n-butyl methacrylate) Diblock Copolymer Micelles in an Ionic Liquid: Scaling of Core and Corona Size with Core Block Length" *Macromolecules* 49 (2016) pp. 3639-3646.
Mai, et al. "Self-assembly of block copolymers" *Chem. Soc. Rev.* 41 (2012) pp. 5969-5985.
Maysinger, et al. "Fate of micelles and quantum dots in cells" *Eur. J. Pharm. Biopharm.* 65 (2007) pp. 270-281.
Murov "Common Solvents Used in Organic Chemistry: Table of Properties" (2016) *ACS Div. Org. Chem.* (2016) pp. 1-2.
Murphy, et al. "Unlocking Chain Exchange in Highly Amphiphilic Block Polymer Micellar Systems: Influence of Agitation" *ACS Macro Lett.* 3 (2014) pp. 1106-1111.
Person, et al. "Catalytic Y-tailed amphiphilic homopolymers—aqueous nanoreactors for high activity, low loading SCS pincer catalysts" *Polym. Chem.* 4 (2013) pp. 2033-2039.
Peters, et al. "Nanostructured Antimony-Doped Tin Oxide Layers with Tunable Pore Architectures as Versatile Transparent Current Collectors for Biophotovoltaics" *Adv. Funct. Mater.* 26 (2016) pp. 6682-6692.
Radiolab. "Bigger Than Bacon podcast" *WNYC Studios* May 9, 2016. http://www.radiolab.org/story/bigger-bacon/ (Web only).
Rauda, et al. "General method for the synthesis of hierarchical nanocrystal-based mesoporous materials" *ACS Nano* 6 (2012) pp. 6386-6399.
Rharbi, et al. "Temperature dependence of fusion and fragmentation kinetics of Triton X-100 micelles" *J. Am. Chem. Soc.* 122 (2000) pp. 6242-6251.
Suslick, et al. "Inside a Collapsing Bubble: Sonoluminescence and the Conditions During Cavitation" *Ann. Rev. Phys. Chem.* 59 (2008) pp. 659-683.
Suslick, K.S. "Sonochemistry" *Kirk-Othmer Encycl. Chem. Techn.* John Wiley & Sons, Inc. (2000) pp. 1-21.
Suslick, K.S. "The Chemical Effects of Ultrasound" *Sci. Am.* 260 (1989) pp. 80-86.
Tang, et al. "Synthesis of nitrogen-doped mesoporous carbon spheres with extra-large pores through assembly of diblock copolymer micelles" *Angew. Chem.* 54 (2015) pp. 588-593.
Wang, et al. "Role of amphiphilic block copolymer composition on pore characteristics of micelle-templated mesoporous cobalt oxide films" *Langmuir* 32 (2016) pp. 4077-4085.
Won, et al. "Molecular exchange in PEO—PB micelles in water" *Macromolecules* 36 (2003) pp. 953-955.
International Searching Authority. International Search Report & Written Opinion. PCT Appl. No. PCT/US2017/050158 (dated Nov. 16, 2017) pp. 1-9.

\* cited by examiner

ULTRASONIC CAVITATION ENABLED TUNING OF PERSISTENT MICELLES

RELATED APPLICATIONS

The present application is the national stage entry of International Patent Application No. PCT/US2017/050158, filed on Sep. 6, 2017, which claims priority to U.S. Provisional Patent Application Ser. No. 62/481,822, filed on Apr. 5, 2017, both of which are incorporated herein in their entirety by reference thereto.

BACKGROUND

Selective solvents drive the aggregation of block copolymers to self-assemble into micelles that partition the solvophobic block into the core of the micelle. Micelles have been widely employed for emulsions, drug delivery, nanoreactors, and soft-templates for diverse materials. In each of these examples, the size of the micelle largely influences the performance. Micelles of diverse dimensions are needed for different applications. For drug delivery, the micelle's size determines both the loading capacity as well as the capability to cross cell membranes. In the case of micelle templated bioelectrodes, the pore size must balance the need for surface area enhancement against the need for large enough pores to accommodate biological photoactive species. For example, high molar mass block copolymer micelles can generate about 80 nanometer macropores in antimony-doped tin oxide electrodes. With micelle size playing a key role in numerous applications, the capability to kinetically trap a desired persistent micelle size would be beneficial. For example, persistent micelle templating (PMT) uses kinetically trapped micelles for the fabrication of highly tunable porous materials with independent control over both the pore size and the material wall thickness. The use of kinetic entrapment to prevent micelles from responding to changing solution conditions is crucial to decouple the resulting pore size from an adjustable wall thickness. The production of persistent micelles has been shown to be predictable from a thermodynamic perspective of the solution conditions.

Block copolymer micelles generally evolve through single chain exchange, micelle fusion/fission, or a combination of these processes. The rate of exchange varies strongly with the thermodynamic barrier for rearrangement. For single-chain exchange, there is a double exponential rate dependence on $\chi N$, where $\chi$ is the high Flory-Huggins effective interaction parameter between the solvent and the solvophobic block and N is the solvophobic block length. For example, one study has found that a high-$\chi N$ system of poly(ethylene oxide-b-butadiene) in water exhibited negligible chain exchange after eight days. Another study with the same high-$\chi N$ system showed that stirring over many days activated a novel exchange process that resulted in a bimodal distribution of micelles. Further, it was later discovered that agitation-induced chain exchange (AICE) by vortexing was observable over a time period of less than fifteen minutes, where it should be noted that chain exchange is a much faster process than micelle size equilibration. A key finding was that AICE was surface-limited and scaled with the rate of turn-over of the solution-air interface. The strong dependence of exchange rate on agitation was recently shown to be a novel method to tune micelle size distributions and then kinetically trap persistent micelles under high-$\chi N$ conditions. It has also been shown that the application of ultrasonic waves to solutions induces continuous cavitation events to form less than 200 micrometer (μm) diameter bubbles (where the diameter varies with sonic power and solution) that collapse on the microsecond timescale and can produce ephemeral conditions with pressures of several hundred atmospheres and temperatures up to 5500° C. For example, the pistol shrimp uses the disruptive power of cavitation to attack prey.

In the specific case of micelle solutions, what is needed is a faster chain exchange and faster changes of micelle size populations compared to vortexing. Although increased AICE by vortexing was observable over a time period of less than fifteen minutes, a more efficient, faster method of AICE would be useful.

SUMMARY OF THE INVENTION

In one embodiment of the present invention, a method of adjusting an average core diameter of persistent micelles is provided. The method includes dissolving a polymer in a solvent to form a solution containing the persistent micelles and subjecting the solution to ultrasonic cavitation.

In one particular embodiment, the polymer can be a block copolymer comprising a first polymer block and a second polymer block. The block copolymer can have a molar mass between about 1 kilogram mol$^{-1}$ and about 1500 kilograms mol$^{-1}$. Further, the Flory-Huggins effective interaction parameter between the first polymer block and the second polymer block can range from about 0.01 to about 5. In addition, the first polymer block can include a polyether, and the second polymer block can include an acrylate. For instance, the block copolymer can include poly(ethylene oxide-b-hexyl acrylate).

In another embodiment, the first solvent can be a selective solvent that is selective for the first polymer block or the second polymer block. For instance, the first solvent can include water.

In yet another embodiment, the method can include adding a second solvent to the solution, wherein the second solvent can be a selective solvent selective for the first polymer block or the second polymer block.

In still another embodiment, the first solvent can be anhydrous. For example, the first solvent can include anhydrous tetrahydrofuran. Meanwhile, the second solvent can include water.

In an additional embodiment, the second solvent can introduce from about 1 volume % to about 99.5 volume % of water to the solution.

In one more embodiment, the ultrasonic cavitation can facilitate AICE between the persistent micelles to increase the average core diameter of the persistent micelles.

In another embodiment, the ultrasonic cavitation can be carried out for a time period ranging from about 1 second to about 10 days.

In still another embodiment, the ultrasonic cavitation can be continuous.

In another embodiment, the ultrasonic cavitation can create and eliminate solution-gas interfaces to accelerate AICE.

In yet another embodiment, the ultrasonic cavitation can be carried out at a power level ranging from about 150 watts to about 300 watts.

In still another embodiment, subjecting the solution to the ultrasonic cavitation can increase the extent of AICE compared to vortexing.

In one more embodiment, the average core diameter of the persistent micelles can range from about 26 nanometers to about 30 nanometers.

In an additional embodiment, the present invention contemplates a drug delivery dispersion that includes persistent micelles, wherein an average core diameter of the persistent micelles is adjusted according to the method described above.

In another embodiment, the present invention contemplates a mesoporous or macroporous film containing a plurality of pores having an average pore diameter. The average pore diameter corresponds to an average core diameter of persistent micelles, wherein the average core diameter of the persistent micelles is adjusted according the method described above, wherein the mesoporous or macroporous film is formed by adding a mesoporous or macroporous film precursor to the solution after ultrasonic cavitation.

In one particular embodiment, the mesoporous or macroporous film can include an oxide, a nitride, a carbide, a metal, or a carbon material. For example, the mesoporous or macroporous film can include niobium pentoxide, tungsten trioxide, titanium dioxide, tin dioxide, or silicon dioxide.

Other features and aspects of the present invention are set forth in greater detail below.

BRIEF DESCRIPTION OF THE DRAWINGS

A full and enabling disclosure of the present invention, including the best mode thereof to one skilled in the art, is set forth more particularly in the remainder of the specification, which includes reference to the accompanying Figures.

Figure 1:
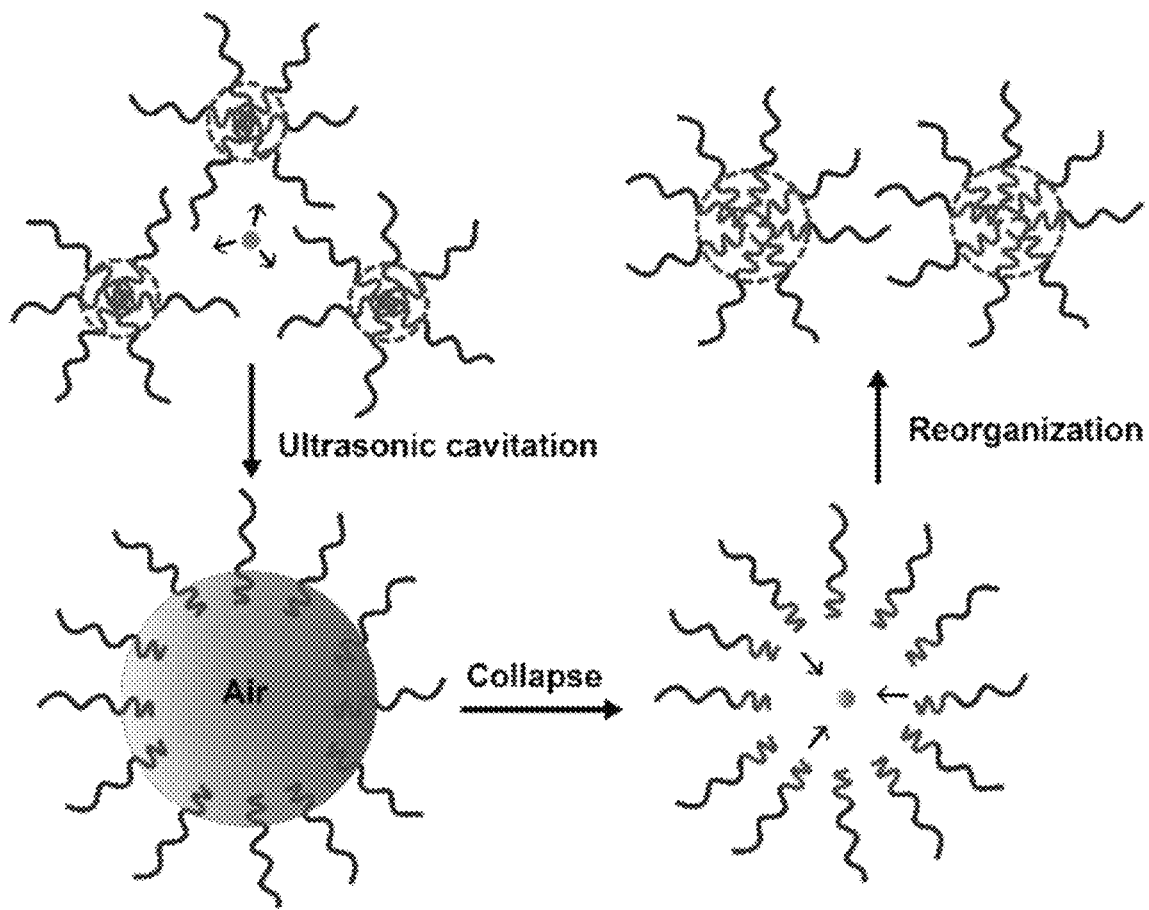
FIG. 1 shows the process of using ultrasonic cavitation to create and eliminate solution-gas interfaces to accelerate agitation-induced chain exchanged (AICE) between block copolymer micelles under high-$\chi$N solution conditions.

Repeat use of reference characters in the present specification and drawings is intended to represent the same or analogous features or elements of the present invention.

DETAILED DESCRIPTION

Reference now will be made to the embodiments of the invention, one or more examples of which are set forth below. Each example is provided by way of an explanation of the invention, not as a limitation of the invention. In fact, it will be apparent to those skilled in the art that various modifications and variations can be made in the invention without departing from the scope or spirit of the invention. For instance, features illustrated or described as one embodiment can be used on another embodiment to yield still a further embodiment. Thus, it is intended that the present invention cover such modifications and variations as come within the scope of the appended claims and their equivalents. It is to be understood by one of ordinary skill in the art that the present discussion is a description of exemplary embodiments only, and is not intended as limiting the broader aspects of the present invention, which broader aspects are embodied exemplary constructions.

Generally, the size (e.g., average core diameter) of a micelle size determines how it performs in various applications. As such, the ability to utilize methods and conditions that prevent micelles from changing their size, where the micelles are referred to as "persistent micelles," has many advantages. However, the adjustment of micelles under such conditions is very difficult. In order to address this problem, the present invention is directed a method to quickly adjust the size of micelles and then return the micelles to a persistent state. Specifically, the present invention is directed to a method for block copolymer micelle growth under high-$\chi$N solution conditions where ultrasonic cavitation facilitates rapid solution-gas interface production that accelerates micelle growth by an order of magnitude over other methods such as vortexing. The persistent micelles of the present invention can then be used for controlled delivery of dispersions in organic electronic coatings, paint, or drug delivery applications and can also be used to control the pore size of inorganic films such as niobium pentoxide, tungsten trioxide, titanium dioxide, tin dioxide, or silicon dioxide mesoporous or macroporous films. Further, it is to be understood that the present invention contemplates the use of persistent micelles in conjunction with films that include an oxide, a nitride, a carbide, a metal, or a carbon material.

In particular, the method of adjusting an average core diameter of persistent micelles contemplated by the present invention includes dissolving a polymer in a solvent to form a solution, adding a water source to the solution, and subjecting the solution to ultrasonic cavitation. The method can be carried out at a temperature ranging from about 20° C. to about 25° C. or any other suitable temperature. The solution can be subjected to ultrasonic cavitation for a time period ranging from about 1 second to about 10 days, such as from about 10 seconds to about 1 day, such as from about 20 seconds to about 12 hours, such as from about 30 seconds to about 10 minutes, such as from about 60 seconds to about 8 minutes, such as from about 90 seconds to about 6 minutes. In one particular embodiment, the solution can be subjected to ultrasonic cavitation for a time period ranging from about 2 minutes to about 5 minutes. Further, ultrasonic cavitation can be carried out at a power level ranging from about 150 watts to about 300 watts, such as from about 175 watts to about 275 watts, such as from about 200 watts to about 250 watts. The persistent micelles formed as a result of the ultrasonic cavitation step can have an increased average core diameter compared to micelles formed via other methods for the same time period or longer, such as vortexing. For example, the persistent micelles formed according to the methods contemplated by the present invention can have an average core diameter ranging from about 26 nm to about 30 nm, such as from about 26.5 nm to about 29.5 nm, such as from about 27 nm to about 29 nm.

Any suitable polymer can be used as the base polymer for forming the persistent micelles. In one particular embodiment, the polymer can be a block copolymer. For instance, the polymer can include a first block that includes a polyether (e.g., polyethylene oxide (PEO)) and a second block that includes an acrylate. For example, the block copolymer can be poly(ethylene oxide-b-hexyl acrylate) or poly(ethylene oxide-b-methyl methacrylate). Other suitable block copolymers contemplated by the present invention include polyisoprene-b-PEO and polystyrene-b-PEO, poly(butyl acrylate-b-ethylene oxide), or any other amphiphilic block copolymer. Further, the block copolymer can have a molar mass ranging from about 1 kilogram mol$^{-1}$ to about 1500 kilograms mol$^{-1}$, such as from about 10 kilograms mol$^{-1}$ to about 800 kilograms mol$^{-1}$, such as from about 15 kilograms mol$^{-1}$ to about 400 kilograms mol$^{-1}$, such as from about 20 kilograms mol$^{-1}$ to about 100 kilograms mol$^{-1}$. In addition, the Flory-Huggins effective interaction parameter $\chi N$ between the first polymer block and the second polymer block can range from about 0.01 to about 5, such as from about 0.1 to about 2.5, such as from about 0.2 to about 1, such as from about 0.30 to about 0.40, such as from about 0.32 to about 0.38, such as from about 0.33 to about 0.37.

Regardless of the particular polymers used to form the persistent micelles according to the method contemplated by the present invention, the solution from which the persistent micelles are formed can include a first solvent and a second solvent, where the second solvent can be a selective solvent that induces micellization and kinetic entrapment. The first solvent can be anhydrous and can, in one particular embodiment, included anhydrous tetrahydrofuran. The selective solvent can be water or any other liquid (e.g., aqueous hydrochloric acid) that is selective for one polymer block. Further, it is to be understood that the use of two solvents is not necessary in instances where a selective solvent may be used in its pure state. For mixtures of a first solvent and a second (selective) solvent, the selective solvent can be slowly added to the solution, where the selective solvent is added to the solution in an amount ranging from about 1 volume % to about 99.5 volume %, such as from about 1.5 volume % to about 50 volume %, such as from about 2 volume % to about 20 volume %, such as from about 2.5 volume % to about 10 volume %. However, it is also to be understood that any method may be used in which a kinetically trapped micelle is formed.

The present invention may be better understood with reference to the following example.

Example 1

Example 1 demonstrates the ability to quickly and efficiently tune average pore diameter of a persistent micelle to a desired size via sonication according to the method contemplated by the present invention.

This study used poly(ethylene oxide-b-hexyl acrylate) (PEO-b-PHA) with PEO and PHA molar masses of 20 kg mol$^{-1}$ and 43.5 kg mol$^{-1}$, respectively, and a molar mass dispersity of Đ=1.16. The polymer blocks alone have a high effective interaction parameter $\chi_{PEO/PHA}$=0.34 at room temperature (20° C. to 25° C.). The polymer (22.4 mg) was dissolved in 2 mL of anhydrous THF (>99.9%, Aldrich) and 100 μL of 37 wt. % hydrochloric acid (HCl) (aqueous) (ACS grade, VWR) was added slowly to introduce 2.7 vol. % of water. During this process, kinetically trapped micelles are expected to form before the HCl addition is completed. The aqueous HCl was selected as the water source since the micelle solutions were intended to stabilize metal oxide nanoparticles at a later point. The resulting micelle solutions were either non-agitated, vortexed for 5 minutes, vortexed for 60 minutes, or sonicated for 5 minutes. Agitation was accomplished with a Fisher digital vortex mixer (Cat. no. 0215370) at 2000 rpm or a Fisher ultrasonic bath (Cat. no. FS-28) operated continuously at full power (225 Watts) for 5 minutes. Both processes were started at room temperature. Sonication was visually observed to induce cavitation in sample solutions. The non-agitated solution was inverted three times after adding HCl(aq.). Next, 0.051 mL volume of niobium ethoxide (99.9%, Fisher) was added to each sample followed by mild shaking for 1 hour before films were dip-coated onto silicon wafers at a rate of 4.4 millimeters per second (mm s$^{-1}$) under 20-25% relative humidity (RH).

Figure 2A:
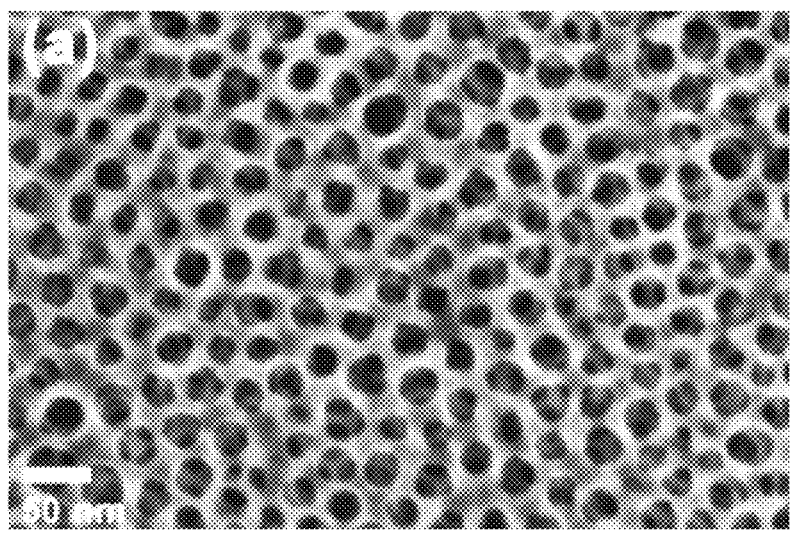
FIG. 2a is a scanning electron microscopy (SEM) image of a porous niobium oxide ($Nb_2O_5$) film templated from micelles that were not agitated.
Figure 2B:
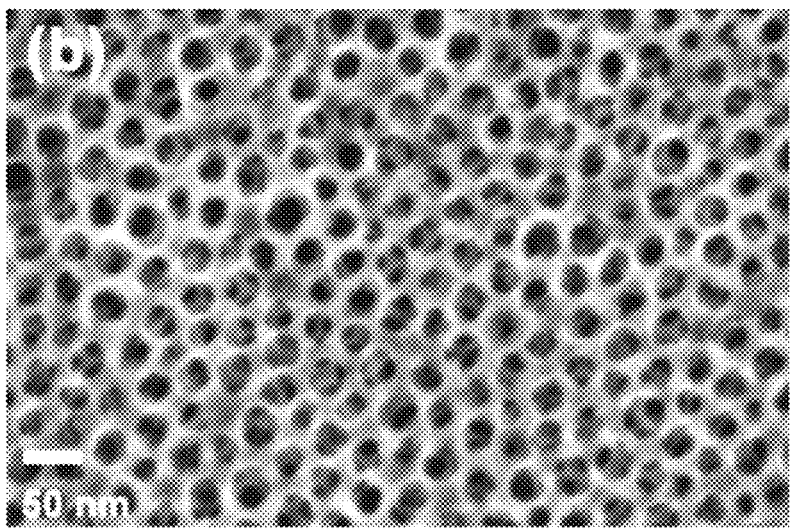
FIG. 2b is an SEM image of a $Nb_2O_5$ film templated from micelles that were agitated by vortexing for 5 minutes.
Figure 2C:
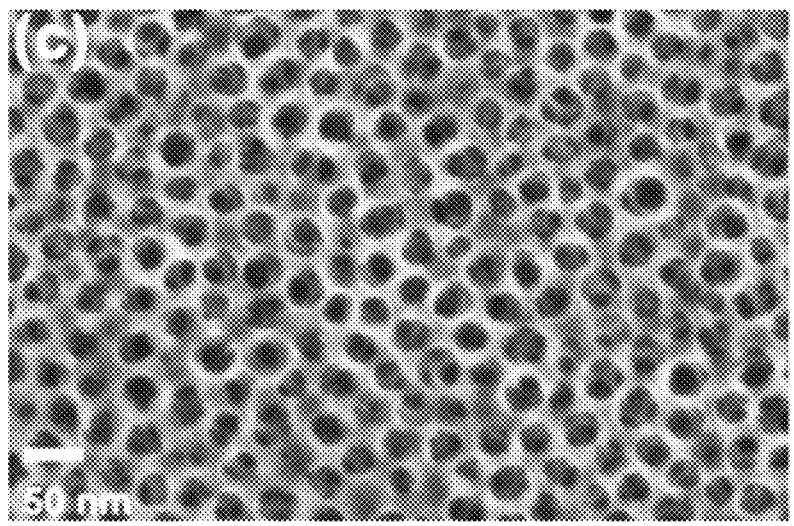
FIG. 2c is an SEM image of a $Nb_2O_5$ film templated from micelles that were agitated by vortexing for 60 minutes.
Figure 2D:
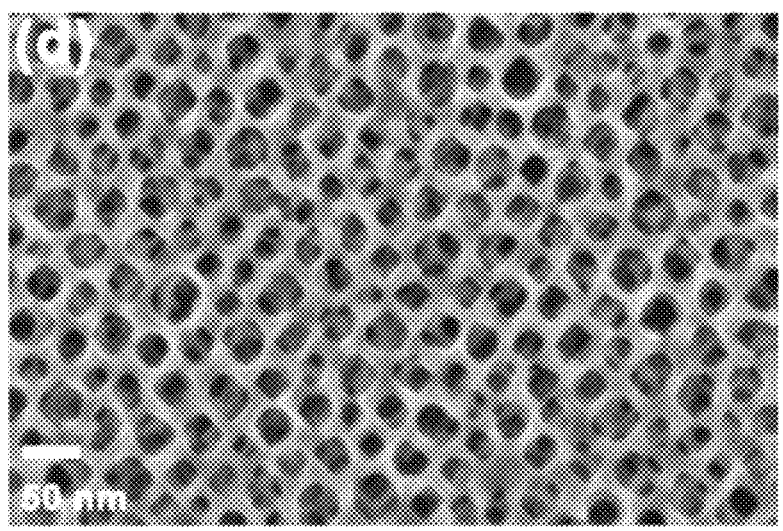
FIG. 2d is an SEM image of a $Nb_2O_5$ film templated from micelles that were agitated by sonication for 5 minutes.

The films were calcined at 600° C. and the resulting porous niobia films were observed by scanning electron microscopy (SEM). Top view images were acquired to determine the in-plane pore diameter statistics using ImageJ. Here, the in-plane pore diameter distribution was used as a proxy for the population of micelle hydrophobic core dimensions. It is noted that the films were largely crack-free, indicating that in-plane periodicity was not distorted as a result of calcination. Thus, SEM pore size measurements may reasonably be used as a high resolution and monotonic proxy for average micelle core diameter. Dynamic light scattering (DLS) was also measured where the micelle hydrodynamic radius changed with the time and the type of agitation. In contrast to DLS, SEM enables the production of high-resolution histograms corresponding to the micelle core dimension alone. SEM images of each sample are shown in FIGS. 2a to 2d and measurement statistics are tabulated in Table 1 below. FIG. 2a is a scanning electron microscopy (SEM) image of a porous niobium oxide ($Nb_2O_5$) film templated from micelles that were not agitated; FIG. 2b is an SEM image of a $Nb_2O_5$ film templated from micelles that were agitated by vortexing for 5 minutes; FIG. 2c is an SEM image of a $Nb_2O_5$ film templated from micelles that were agitated by vortexing for 60 minutes; and FIG. 2d is an SEM image of a $Nb_2O_5$ film templated from micelles that were agitated by sonication for 5 minutes.

TABLE 1

Quantitative measurements of samples by SEM and GISAXS

| | SEM measurements | | GISAXS measurements |
|---|---|---|---|
| Sample name | Average pore[a] diameter (nm) | Standard deviation (nm) | First peak position $q_y$ ($nm^{-1}$) |
| Non-vagitated | 23.2 ± 0.2 | 4.0 | 0.200 |
| Vortex-5 min | 24.1 ± 0.2 | 3.4 | 0.171 |
| Vortex-60 min | 25.8 ± 0.2 | 3.5 | 0.200 |
| Sonicate-5 min | 28.0 ± 0.3 | 4.9 | 0.103 |

[a]Mean ± error of the mean.

Figure 3:
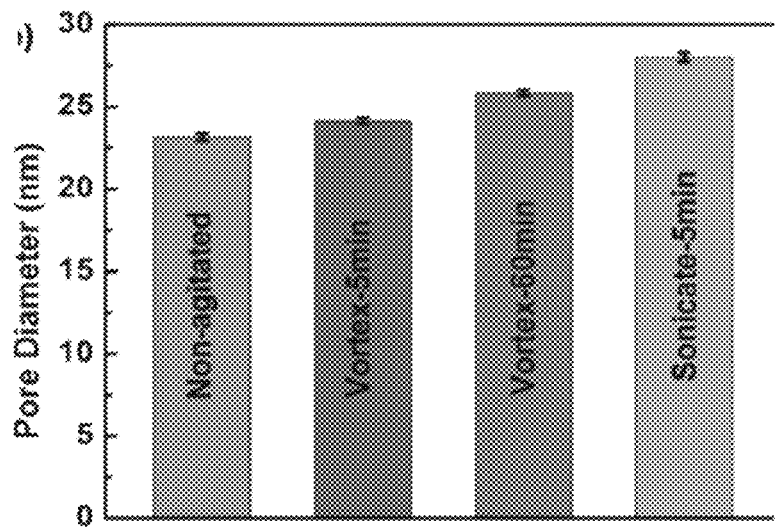
FIG. 3 is a bar graph showing the average pore diameter of micelles that were not agitated, micelles that were vortexed for 5 minutes, micelles that were vortexed for 60 minutes, and micelles that were sonicated for 5 minutes.
Figure 4:
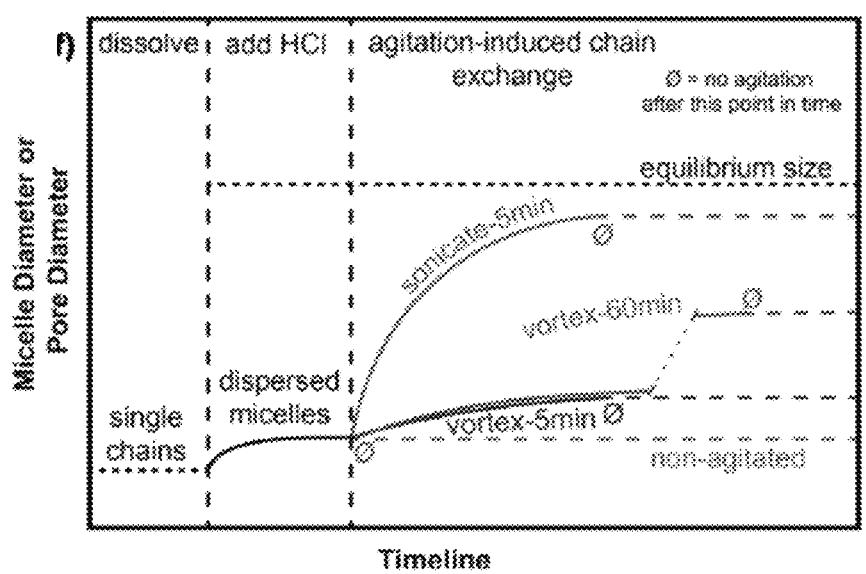
FIG. 4 is a graph illustrating the timeline for solution processing to predict a starting point of persistent micelles below the equilibrium size of the micelles, where the type of agitation determines the rate of change while the agitation time determines the extent of change in the average pore diameter of the micelles.
Figure 5:
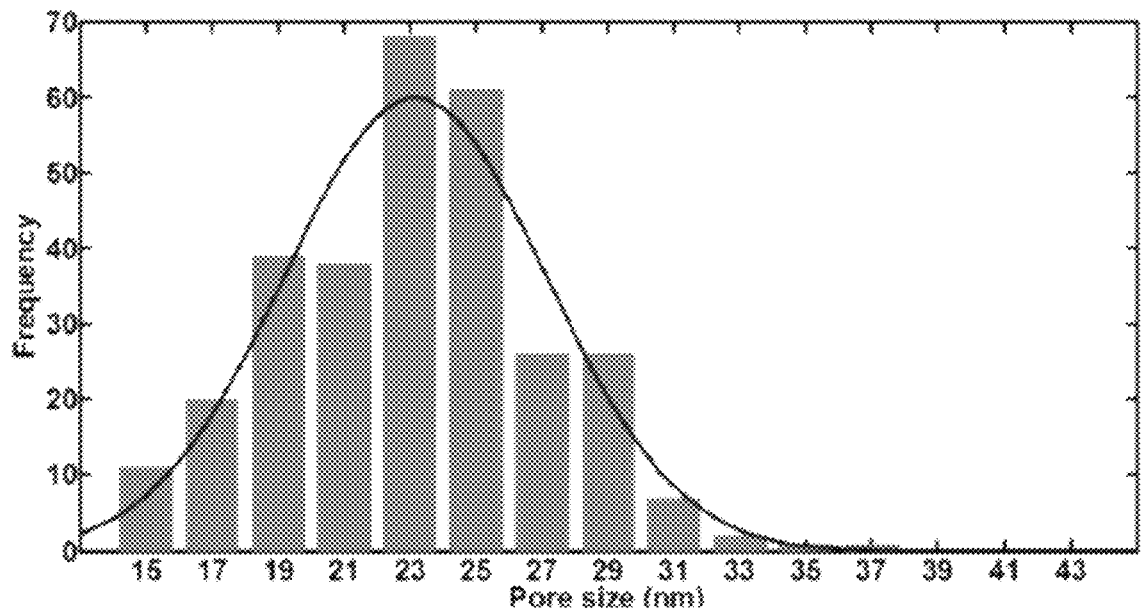
FIG. 5 is a histogram showing the distribution of the pore size in templated films taken from SEM images, where the pore size serves as a proxy for the micelle average core diameter, where the micelles used to template the film were not agitated.
Figure 6:
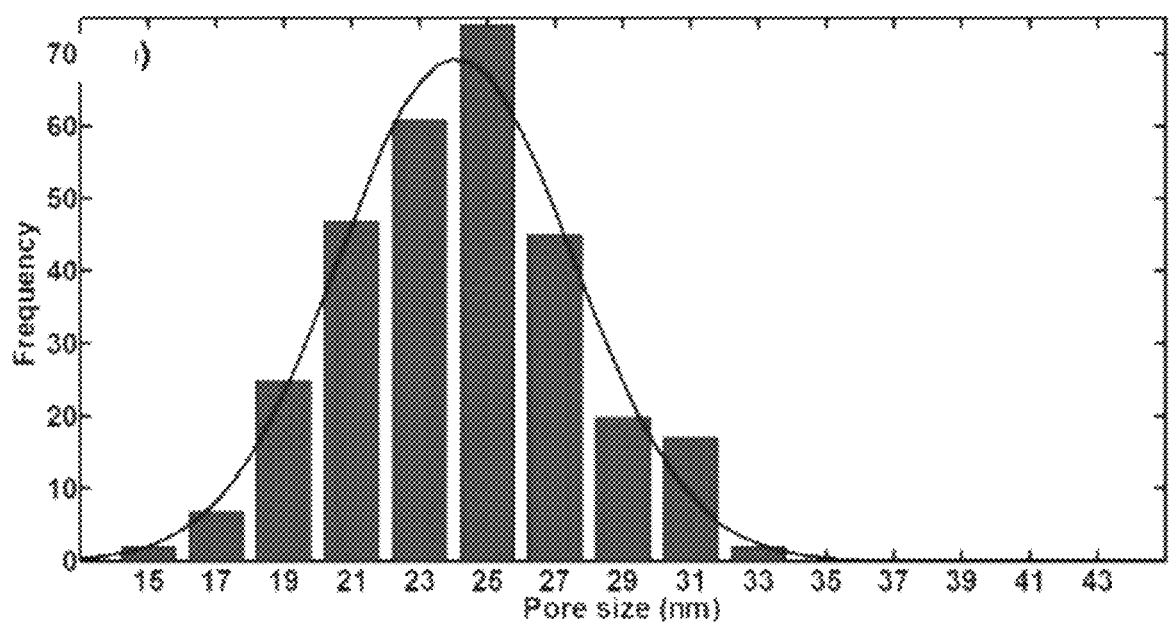
FIG. 6 is a histogram showing the distribution of the pore size in templated films taken from SEM images, where the pore size serves as a proxy for the micelle average core diameter, where the micelles used to template the film were vortexed for 5 minutes.
Figure 7:
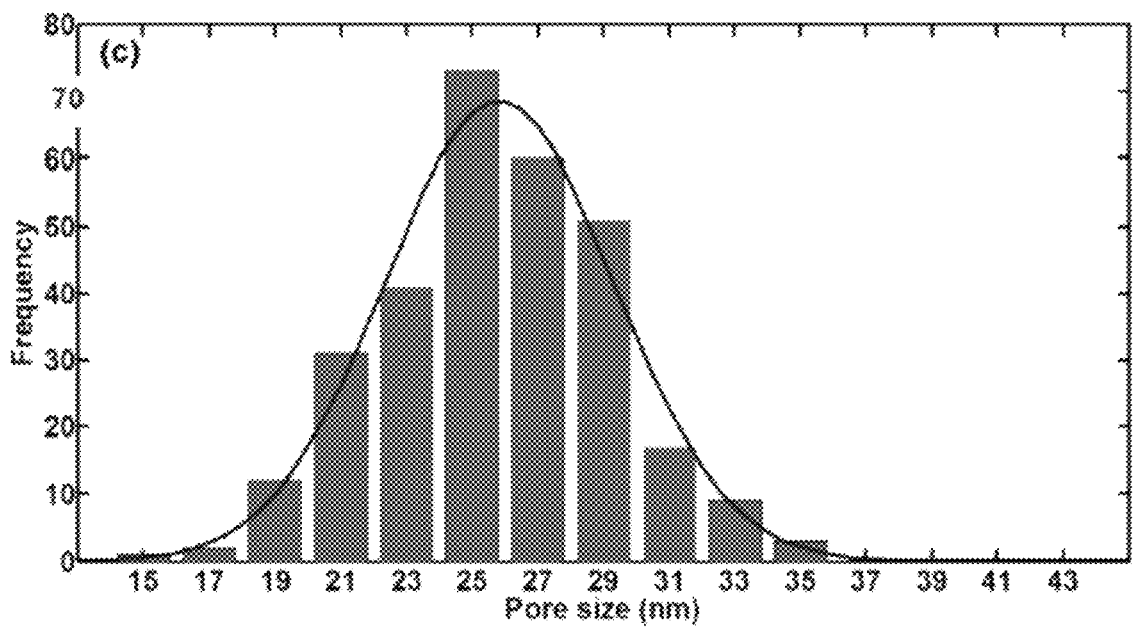
FIG. 7 is a histogram showing the distribution of the pore size in templated films taken from SEM images, where the pore size serves as a proxy for the micelle average core diameter, where the micelles used to template the film were vortexed for 60 minutes.
Figure 8:
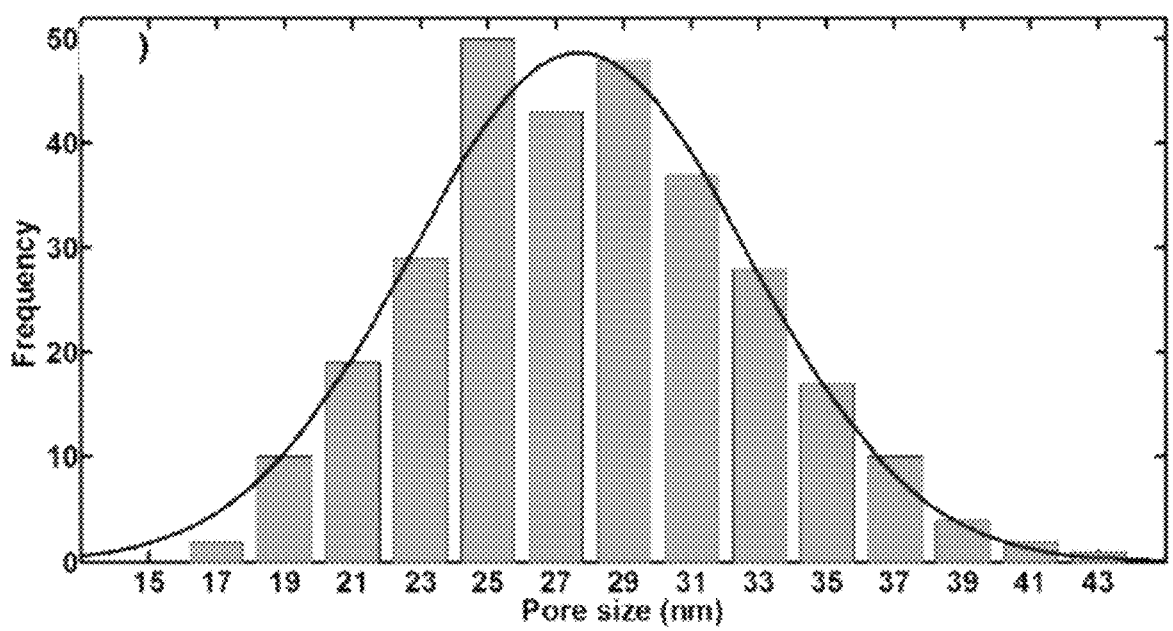
FIG. 8 is a histogram showing the distribution of the pore size in templated films taken from SEM images, where the pore size serves as a proxy for the micelle average core diameter, where the micelles used to template the film were sonicated for 5 minutes.

Block copolymer micelles are generally reported from about 3 nm to about 100 nm, where the combination of $\chi$ and N used in the present example reasonably result in the formation of about 30 nm diameter micelle cores under equilibrium. As shown in Table 1 above, as well as in FIG. 3, the average pore diameter of a film formed from a sample of non-agitated micelles was 23.2±0.2 nm, while the average pore diameter increased from 24.1±0.2 nm to 25.8±0.2 nm for the films formed from samples of micelles that were vortexed for 5 minutes and 60 minutes, respectively. In contrast, sonicating a sample of micelles for 5 minutes resulted in significantly a film having larger pores having an average pore diameter of 28.0±0.3 nm, which is larger than the average pore diameter of the film formed from a sample that was vortexed for a time period 12 times as long (i.e., 60 minutes), where it is to be understood that the average pore diameter of pores in the film corresponds with the average core diameter of the persistent micelle in each sample. See Table 1 and FIG. 3. Histograms of pore size from several hundred data points for each sample were well-fit with single Gaussians, as shown in FIGS. 5 to 8. FIG. 5, is the histogram for the non-agitated sample; FIG. 6 is the histogram for the sample that was vortexed for 5 minutes; FIG. 7 is the histogram for the sample that was vortexed for 60 minutes; and FIG. 8 is the histogram for the sample that was sonicated for 5 minutes. In light of the previously observed bimodal pathway for micelle evolution, it is noted that the statistical width may obscure two convolved distributions that are narrowly separated. The observed micelle growth trends were consistent with exchange towards a larger equilibrium size as shown in FIG. 3. This is expected considering that the micelles become kinetically trapped part way through the initial HCl(aq.) addition. The further increase in water content increases the effective interaction parameter $\chi_{PHA/solution}$, between PHA and the solvent. The corresponding increase in surface tension shifts the balance of surface energy (enthalpy) to chain stretching (entropy) to favor an increased nominal micelle size. The use of high-$\chi$N conditions, however, inhibits quiescent micelles from undergoing chain exchange towards the new equilibrium. See FIG. 4. In the context of AICE, an enhancement of the surface turn-over rate is expected to promote faster chain exchange according to FIG. 1. These results are consistent with faster chain exchange that evolves micelles towards a larger equilibrium size as shown in FIG. 4. Following this model, higher sonication powers are expected to produce surface area faster and thus promote further chain exchange. It is noted that these results are also consistent with the formation of a new micelle size distribution as a result of kinetic-limited processes during rapid surface collapse. In both cases, the extent of surface turnover decreases the fraction of the starting micelle size distribution and increases the relative amount of the new population. Regardless, the use of sonication enables rapid modification of nominal micelle size.

Figure 9A:
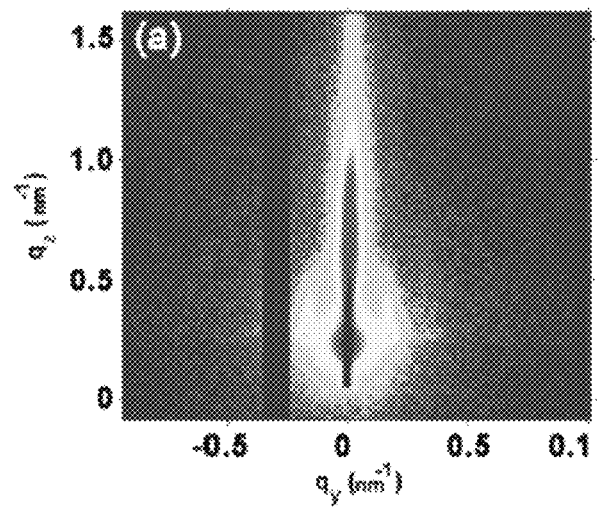
FIG. 9a shows a grazing-incidence small-angle X-ray scattering (GISAXS) measurement of a PEO-b-PHA/$Nb_2O_5$ film at an incidence angle of $\alpha_i=0.22°$, where the micelles used to template the film were not agitated.
Figure 9B:
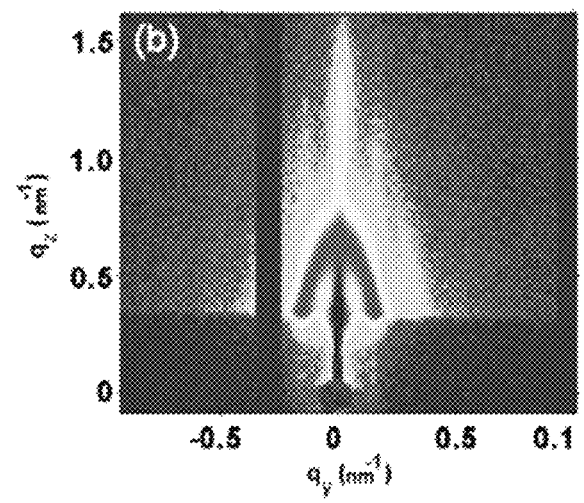
FIG. 9b shows a GISAXS measurement of a PEO-b-PHA/$Nb_2O_5$ film at an incidence angle of $\alpha_i=0.22°$, where the micelles used to template the film were vortexed for 5 minutes.
Figure 9C:
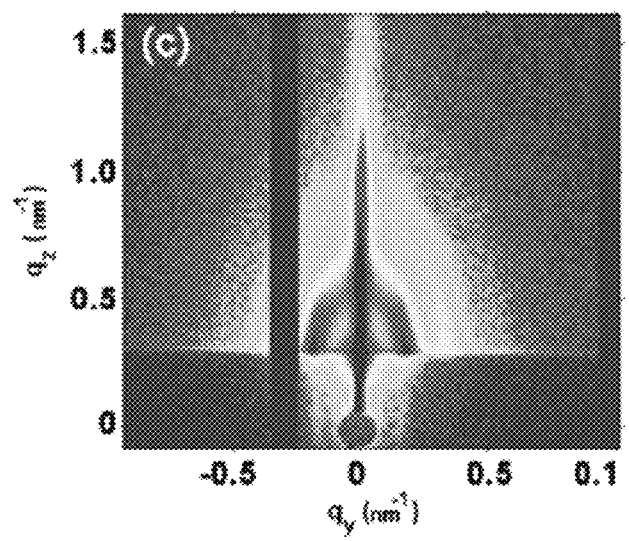
FIG. 9c shows a GISAXS measurement of a PEO-b-PHA/$Nb_2O_5$ film at an incidence angle of $\alpha_i=0.22°$, where the micelles used to template the film were vortexed for 60 minutes.
Figure 9D:
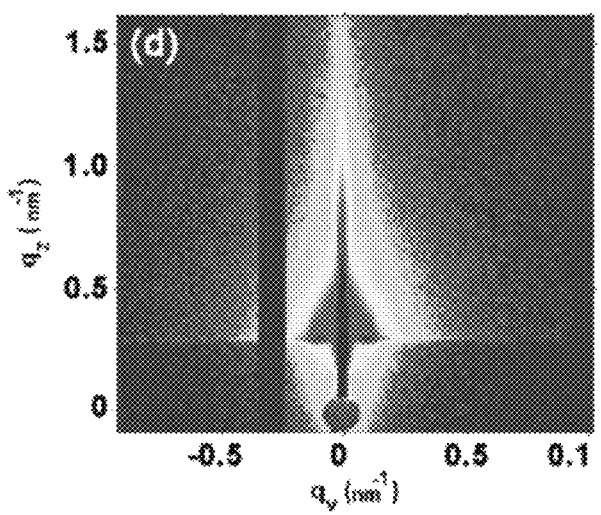
FIG. 9d shows a GISAXS measurement of a PEO-b-PHA/$Nb_2O_5$ film at an incidence angle of $\alpha_i=0.22°$, where the micelles used to template the film were sonicated for 5 minutes.
Figure 9E:
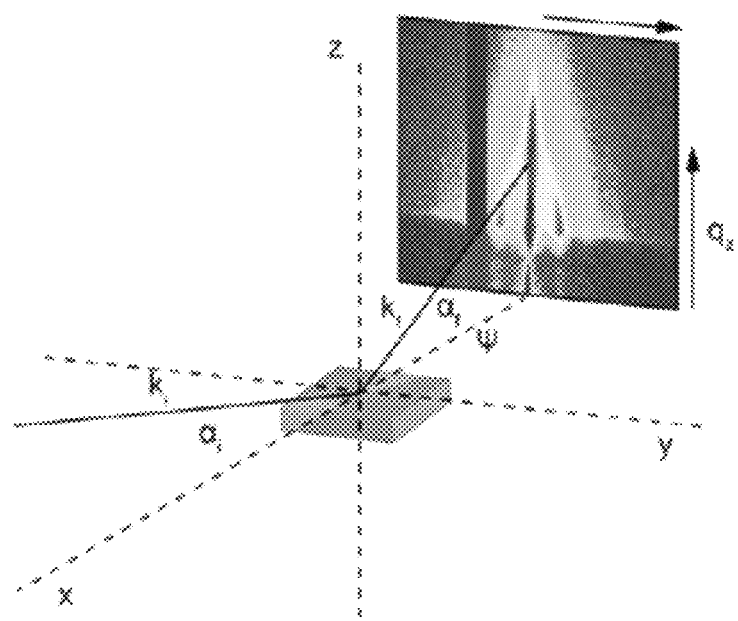
FIG. 9e is a schematic illustrating the sample measurement geometry used for the measurements in FIGS. 9a to 9d.
Figure 10:
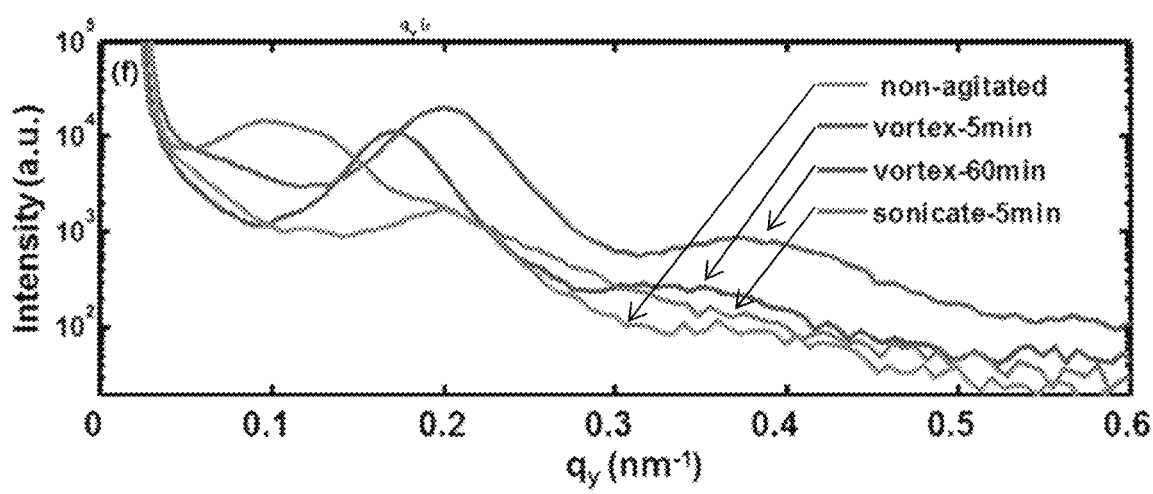
FIG. 10 is a graph comparing the in-plane cutes of scattering intensity for each of the films in FIGS. 9a to 9d.

Grazing-incidence small-angle X-ray scattering (GISAXS) was used as an ensemble measurement to further quantify changes to film morphologies. Line cuts of in-plane scattering intensity were extracted from each 2D image to quantify in-plane periodicity according to FIG. 10. Compared to sample non-agitated, both the 5-minute sonication sample and the 5-minute vortex sample exhibited first peaks shifted to lower-q, monotonically corresponding to the increase in feature sizes observed by SEM (Table 1). As shown in FIGS. 9b and 9c, the 2D data were similar for both vortexed samples and indicated significant long-range order with multiple in-plane correlations as well as out-of-plane correlations. In contrast, and as shown in FIGS. 9a and 9d, the 2D data from the non-agitated sample and the 5-minute sonication sample predominantly exhibited in-plane correlations. FIG. 9e shows a schematic of the sample measurement geometry used for FIGS. 9a to 9d. The decreased long-range order for the non-agitated sample and the 5-minute sonication sample may be due to the larger relative micelle size distributions (du) that inhibit the packing of highly ordered lattices. It is noted that 60-minute vortex sample curiously exhibited a decreased apparent lattice constant by GISAXS and an increased pore size by SEM. This unexpected lattice contraction with larger micelle populations may be associated with the varying relative standard deviation changing the resulting packing density. For all samples, the strong in-plane scattering observed by GISAXS indicates changes to well-defined morphologies.

In addition, the inorganic crystal structure and crystallite sizes were examined by wide-angle diffraction after calcination. The observed reflections were consistent with orthorhombic $Nb_2O_5$ (PDF no. 27-1003) with a nominal grain size of 12 nm to 15 nm. The demonstrated micelle tuning is generalizable to different inorganic systems since the micelle size tuning is performed before the addition of the inorganic material. The micelle templating of tungsten trioxide ($WO_3$) after AICE demonstrated the ability to control film formation of multiple inorganic materials.

It is believed that this is the first example of ultrasonic cavitation promoting the rapid growth of block copolymer micelles under high-$\chi$N solution conditions. The results here demonstrate rapid micelle growth by sonication under kinetically challenging high-$\chi$N solution conditions. In the absence of agitation, such persistent micelles offer numerous benefits where a desired micelle size may be tuned first with AICE and then maintained constant despite changing solution conditions. Compared to vortexing, the rapid micelle growth with sonication as shown in FIG. 1 was attributed to an enhancement of the solution-air interface turn-over rate. These findings demonstrate more than an order of magnitude faster micelle growth by sonication as compared to vortexing alone.

These and other modifications and variations to the present invention may be practiced by those of ordinary skill in the art, without departing from the spirit and scope of the present invention, which is more particularly set forth in the appended claims. In addition, it should be understood the aspects of the various embodiments may be interchanged both in whole or in part. Furthermore, those of ordinary skill in the art will appreciate that the foregoing description is by way of example only, and is not intended to limit the invention so further described in the appended claims.

What is claimed is:

1. A method of adjusting an average core diameter of persistent micelles, the method comprising:
   dissolving a block polymer in a first solvent to form a solution containing micelles;
   adding a second solvent to the solution to increase an interaction parameter $\chi$ between a block polymer in a core of each of the micelles and the solution until chain exchange processes are halted, resulting in the formation of persistent micelles, wherein the average core diameter of the persistent micelles does not change when quiescent; and
   subjecting the solution of persistent micelles to ultrasonic cavitation to temporarily form non-persistent micelles via agitation-induced chain exchange between the non-persistent micelles to adjust the average core diameter, wherein the non-persistent micelles are returned to a persistent state after the ultrasonic cavitation, preventing subsequent changes to their average core diameter.

2. The method of claim 1, wherein the block polymer comprises a first polymer block and a second polymer block.

3. The method of claim 1, wherein the block copolymer has a molar mass between about 1 kilogram mol$^{-1}$ and about 1500 kilograms mol$^{-1}$.

4. The method of claim 2, wherein the Flory-Huggins effective interaction parameter between the first polymer block and the second polymer block ranges from about 0.01 to about 5.

5. The method of claim 2, wherein the first polymer block comprises a polyether and the second polymer block comprises an acrylate.

6. The method of claim 5, wherein the block copolymer comprises poly(ethylene oxide-b-hexyl acrylate).

7. The method of claim 2, wherein the first solvent is a selective solvent selective for the first polymer block or the second polymer block.

8. The method of claim 7, wherein the first solvent comprises water.

9. The method of claim 1, wherein the second solvent is a selective solvent selective for the first polymer block or the second polymer block.

10. The method of claim 9, wherein the first solvent is anhydrous.

11. The method of claim 10, wherein the first solvent comprises anhydrous tetrahydrofuran.

12. The method of claim 9, wherein the second solvent comprises water.

13. The method of claim 9, wherein the second solvent introduces from about 1 volume % to about 99.5 volume % of water to the solution.

14. The method of claim 1, wherein the ultrasonic cavitation is carried out for a time period ranging from about 1 second to about 10 days.

15. The method of claim 1, wherein the ultrasonic cavitation is continuous.

16. The method of claim 1, wherein the ultrasonic cavitation creates and eliminates solution-gas interfaces to accelerate agitation induced chain exchange.

17. The method of claim 1, wherein the ultrasonic cavitation is carried out at a power level ranging from about 150 watts to about 300 watts.

18. The method of claim 1, wherein subjecting the solution of persistent micelles to the ultrasonic cavitation increases the extent of agitation-induced chain exchange compared to vortexing.

19. The method of claim 1, wherein the average core diameter of the persistent micelles ranges from about 26 nanometers to about 30 nanometers.

* * * * *